United States Patent
Hidalgo et al.

(10) Patent No.: US 9,157,877 B2
(45) Date of Patent: Oct. 13, 2015

(54) METHOD FOR CHARACTERIZING AN ETHYLENE AND VINYL ACETATE COPOLYMER

(75) Inventors: Manuel Hidalgo, Brignais (FR); Franck Medlege, Meylan (FR)

(73) Assignees: ARKEMA FRANCE, Colombes (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 52 days.

(21) Appl. No.: 14/117,416

(22) PCT Filed: Mar. 2, 2012

(86) PCT No.: PCT/FR2012/050440
§ 371 (c)(1),
(2), (4) Date: Nov. 13, 2013

(87) PCT Pub. No.: WO2012/160279
PCT Pub. Date: Nov. 29, 2012

(65) Prior Publication Data
US 2014/0334515 A1     Nov. 13, 2014

(30) Foreign Application Priority Data
May 26, 2011 (FR) ...................... 11 54579

(51) Int. Cl.
*G01N 25/48* (2006.01)
*G01N 25/20* (2006.01)
*G01N 33/44* (2006.01)

(52) U.S. Cl.
CPC ............. *G01N 25/48* (2013.01); *G01N 25/4866* (2013.01); *G01N 25/20* (2013.01); *Y10T 436/200833* (2015.01); *Y10T 436/216* (2015.01)

(58) Field of Classification Search
CPC ....... G01N 25/00; G01N 25/20; G01N 25/48; G01N 25/4866; Y10T 436/20; Y10T 436/200833; Y10T 436/21; Y10T 436/216
USPC ......... 436/127, 128, 139, 142, 147; 422/68.1, 422/82.12, 51; 374/10
See application file for complete search history.

(56) References Cited

FOREIGN PATENT DOCUMENTS

WO    2012/006837    *   1/2012

OTHER PUBLICATIONS

Zhiyong Xia et al., A new method for measuring cross-link density in ethylene vinyl acetate-based encapsulant, BP Solar Internationa, Inc., Frederick, Maryland, USA www.pv-tech.org, pp. 150-159.
O. Bianchi et al., Assessment of Avrami, Ozawa and Avrami-Ozawa equations for determination of EVA crosslinking kinetics from DSC measurements, Polymer Testing 27, 2008, pp. 722-729.
Trenton E. Gould et al., Characterization of mouthguard materials: Thermal properties of commercialized products, Dental Materials vol. 25, No. 12, Dec. 1, 2009, pp. 1593-1602.
J.A. Reyes-Labarta et al., DSC and TGA study of the transitions involved in the thermal treatment of binary mixtures of PE and EVA copolymer with a crosslinking agent, Polymer, Elsevier Science Publishers B.V., GB, vol. 47, No. 24, Nov. 8, 2006, pp. 8194-8202.
Heng-Yu Li et al., Towards in-line determination of EVA Gel Content during P"V modules Lamination Processes, Proceedings of the 25$^{th}$ PVSC Conference, Jan. 1, 2010, 3 pages.
W. Stark et al., Investigation of Ethylene/Vinyl Acetate Copolymer (EVA) by thermal analysis DSC and DMA, Polymer Testing, vol. 30, No. 2, Dec. 29, 2010, pp. 236-242.
Frank H. Meng et al., Differential scanning calorimetry (DSC) and temperature-modulated DSC study of three mouthguard materials, Dental Materials, Elsevier, vol. 23, No. 12, Nov. 1, 2007, pp. 1492-1499.
C. Sandu et al., Modeling differential scanning calorimetry, Thermochimica Acta, vol. 159, No. 1, Jan. 1, 1990, pp. 267-298.

* cited by examiner

*Primary Examiner* — Maureen Wallenhorst
(74) *Attorney, Agent, or Firm* — Buchanan Ingersoll & Rooney P.C.

(57) ABSTRACT

A process for characterizing a copolymer of ethylene and vinyl acetate (EVA) using a differential calorimetry analysis technique. This process is determining one or more values of characteristic(s) of a sample of EVA copolymer, one of which is a level of crosslinking of the sample. The process makes it possible to determine not only the degree of crosslinking, but also the vinyl acetate content and the molecular mass of an EVA sample, in a simple, rapid, easy and precise manner.

15 Claims, 7 Drawing Sheets

METHOD FOR CHARACTERIZING AN ETHYLENE AND VINYL ACETATE COPOLYMER

Figure 1A:
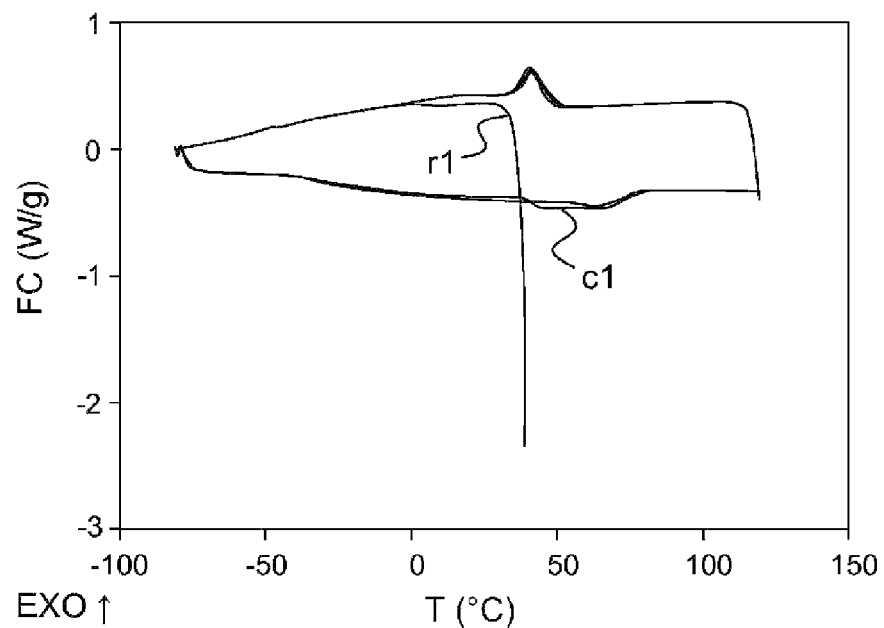

The present invention relates to the field of copolymers of ethylene and vinyl acetate. The term "copolymer of ethylene and vinyl acetate" means any copolymer based on these two monomers as main or majority components. Thus, the term "copolymers of ethylene and vinyl acetate" also comprises copolymers derived from 3 comonomers (terpolymers) or more, in which ethylene and vinyl acetate are the two main or majority monomers.

More particularly, the invention relates to a process for characterizing a copolymer of ethylene and vinyl acetate using a differential calorimetry analysis technique. The invention also relates to a differential calorimetry analysis device, a computer program, a process for controlling the quality of a copolymer of ethylene and vinyl acetate used in the manufacture of a photovoltaic module or cable, and finally a process for controlling the resistance over time of a copolymer of ethylene and vinyl acetate used in the manufacture of a photovoltaic module.

Certain industrials using and crosslinking at the same time films or granules of a copolymer of ethylene and vinyl acetate (noted EVA hereinbelow) have a need to know, in absolute or relative terms, the degree of progress of the crosslinking reaction of the copolymer. They may also need to know the proportion of vinyl acetate in the copolymer, or alternatively its fluidity or its molecular mass, the latter two characteristics being intimately linked. Specifically, the mechanical, thermal and optical properties of EVA copolymers arise especially from the degree of crosslinking, but also from the proportion of vinyl acetate present, or alternatively from the molecular mass. Among these industrials, examples that may be mentioned include cable manufacturers or photovoltaic module manufacturers.

In the field of photovoltaic modules, the process for manufacturing photovoltaic modules that is the most commonly used, according to the crystalline silicon technology, consists in stacking the various constituent layers of the module (front face/encapsulator/photovoltaic cells/encapsulator/rear face) and then in laminating the stack under vacuum in a laminator. In the laminator, the encapsulating EVA melts, covers the photovoltaic cells and then crosslinks to acquire its final damping crosslinked network structure. Thus, the photovoltaic cells are completely encapsulated in a relatively soft rubbery polymer which isolates them from the environment and protects them against impacts and mechanical stresses. During functioning, the temperature of the photovoltaic modules may reach or exceed 100° C. Consequently, in order optimally to ensure its functions in protecting the cells, EVA must have good thermomechanical resistance, which necessitates a sufficient degree of crosslinking. Specifically, the crosslinking of EVA makes it possible to prevent it from undergoing either cold or hot creep. Furthermore, if the EVA is poorly crosslinked, excessive amounts of crosslinking agent remain, in general organic peroxides. Now, an excessive residual amount of these organic peroxides in the EVA may result in premature aging of the photovoltaic modules by degradation of the materials, especially the polymers, due to the possible chemical reactions with the peroxides (such as oxidation) or the decomposition products thereof. This premature aging may be reflected by mechanical, electrical or optical defects, for instance yellowing. Finally, during lamination, the characteristics and the formulation of the EVA used, for instance the type and concentration of the crosslinking agent present, and also the operating conditions such as the vacuum, the temperature and the lamination time in one or more sequences, are variables that may lead to different degrees of crosslinking for the EVA. The knowledge and control of the degree of crosslinking of the EVA-based encapsulator, and of the properties arising therefrom, are therefore very important for the module manufacturer.

The EVA used by the photovoltaic industry is a copolymer comprising a proportion of vinyl acetate and having a molecular mass such that the copolymer has good fluidity during use, i.e. before its crosslinking, and also good transparency and good mechanical properties after its crosslinking. The formulation and implementation temperature of EVA, for example for the manufacture of films, is a direct consequence of its composition and its fluidity. It is particularly important for this temperature to be adjusted in order to prevent the crosslinking agents of the formulation, for example peroxides, from beginning to crosslink the material at this stage. Commonly used proportions of vinyl acetate are between 24% and 42% by weight and preferably between 28% and 35% by weight, and even more preferably, the proportion is 33% by weight. Consequently, the knowledge and control of the proportion of vinyl acetate in the polymer, and of the properties arising therefrom, are also very important for the module manufacturer.

Several known methods exist for ensuring monitoring of the EVA crosslinking reaction. Adaptation of these methods to perform monitoring during the encapsulation process of photovoltaic cells has been the subject of numerous studies. Among these methods is the solvent swelling method based on the Flory-Huggins-Rehner equation. This method makes it possible, via knowledge of the polymer/solvent interaction parameter (Flory-Huggins parameter $\chi_{12}$), to obtain directly the mole density of chemical crosslinking nodes, v. However, this method involves the handling of solvents, which are often volatile and/or toxic, and the measurements are performed at the swelling equilibrium, which may take a lot of time. Furthermore, since the Flory-Huggins polymer/solvent interaction parameter needs to be well known, this often constitutes a curb on the use of this method. As regards semicrystalline polymers, such as EVA, the swelling at room temperature might be a function of the chemical crosslinking nodes, but also of the physical nodes provided by the crystallinity, which would complicate the analysis of the results or make it necessary to work at elevated temperature. Finally, since this swelling method is based on the swelling of a crosslinked network, it is above all usable for networks that are well crosslinked, but its use for poorly or moderately crosslinked polymers may give rise to substantial errors.

Another existing method consists in measuring mechanical moduli by rheology. This technique also gives direct access to the mole density of crosslinking nodes, $v_m$. It does not require the use of solvents or prior knowledge of the parameters. This method is very sensitive to variations in the degree of crosslinking and requires very little material for the measurements. However, it demands sound knowledge and experience in rheology, and also the use of expensive and sophisticated equipment. The samples must also be carefully prepared and of good quality. They must especially have known dimensions and a constant thickness to ensure good reliability of the measurements. This method is consequently complex to perform.

Due to the drawbacks associated with the direct analysis methods, industrials often use indirect methods that may be correlated to the crosslinking node density. Among these indirect methods, a method that is very well known to those skilled in the art is that of measuring the gel proportion, which consists in measuring the insoluble proportion of a sample of crosslinked polymer. To do this, an attempt is made to dissolve a sample in a solvent, the proportion of the sample which has not dissolved (gel proportion) being considered as a measurement of the degree of crosslinking of the polymer. This method of measuring the gel proportion does not make use of any model whose parameters should be known. It does not require any advanced theoretical knowledge. On the other hand, it involves the handling of solvents. Usually, this method makes it necessary to work at high temperatures. For EVA, in particular, good-quality measurements are obtained only when the extraction is performed at sufficiently high temperatures, to ensure that the crystalline parts of the EVA, not linked to the crosslinked network, dissolve and are not counted as crosslinking insolubles. Furthermore, the solvents used, such as toluene, xylene or tetrahydrofuran, for example, are not free of hazard. They are especially flammable and toxic. Although shorter than the solvent swelling measurements, solvent extractions are operations that require a minimum time of several hours, typically more than 12 hours, without taking into account the time for installation or reconditioning of the solvent extraction tool, and must be performed by qualified staff. The mounted apparatus must be installed in well-ventilated work stations, these work stations being specific to a chemistry laboratory and not being able to be readily installed next to the production tool. The use of solvents also implies the need to reprocess them after use, which gives rise to an appreciable extra operating cost.

A new method using an analysis technique by differential calorimetry DSC (Differential Scanning calorimetry) has been studied as a method for monitoring the degree of crosslinking of EVA to overcome the drawbacks of the known methods. Specifically, such a method has several advantages over the existing analysis methods. In particular, this method does not use any solvent. The DSC apparatus for performing the measurements is much less expensive than rheometers, for example, and is much easier to use, not requiring the users to have a level of expertise.

The DSC analysis technique is a dynamic calorimetric technique which consists in measuring the flow of heat necessary to maintain at the same temperature a closed capsule containing the sample to be analyzed and the same type of capsule closed without sample. In its configuration that is most commonly used, the measurement of the flow of heat is performed across a rising or descending temperature ramp as a function of time. During the temperature sweep, thermal phenomena associated with transformations which the sample undergoes take place. These thermal phenomena are, for example, a phase change, a chemical reaction, or a glass transition for amorphous polymers. During these thermal phenomena, the sample absorbs or evolves heat. The apparatus then compensates for this variation in heat to keep the temperatures of the sample and the reference constant. This is reflected, in the recording of the flow of heat as a function of the temperature, by a difference relative to the baseline. This difference may have different forms and intensities. In the figures described in the examples below and representing thermograms of analyzed samples, the endothermic phenomena are oriented downward while the exothermic phenomena are oriented upward. The phase changes of melting and evaporation type are endothermic phenomena. On the other hand, phase changes of crystallization type, and also the majority of chemical reactions, such as crosslinking or decomposition, are exothermic phenomena. The glass transitions of the polymers correspond to a change in heat capacity and they appear as a jump in the level of the baseline of the thermogram. As regards the shape, apart from the glass transitions which correspond in DSC to jumps in heat capacity, many phenomena are reflected by more or less regular shape peaks in a DSC thermogram. Obviously, the transformations that the sample undergoes may be superposed in a thermogram when they take place at close temperatures.

The article entitled "A new method for measuring crosslink density in ethylene vinyl acetate-based encapsulant" by Zhiyong Xia, Daniel W. Cunningham and John H. Wohlgemuth, published especially on the website www.pv.tech.org, describes this new method for determining the degree of crosslinking of a crosslinkable EVA encapsulator using the DSC analysis technique. This method uses the fact that, for applications such as encapsulating photovoltaic cells, an EVA is virtually always formulated with peroxides to bring about its crosslinking. It is based on the idea that EVA, even after having undergone a lamination cycle to crosslink it, still contains non-decomposed peroxide, known as residual peroxide. The typical proportion of residual peroxide in a crosslinked EVA is estimated at 30% of the peroxide contained in the starting EVA, i.e. before crosslinking. This method thus begins from the principle that the less residual peroxide there is remaining, after lamination, the more the EVA will have crosslinked during this operation. The method consists in monitoring, by DSC, the thermal trace of the peroxide decomposition reaction, this decomposition taking place at temperatures above 100° C., more particularly between 150° C. and 180° C. The DSC measurement first makes it possible to determine the total enthalpy of crosslinking, initiated by the decomposition of the peroxide, by forming the measurement on a "fresh" sample of EVA, i.e. a non-crosslinked EVA which is assumed to have all of its peroxide charge available. It then makes it possible to measure the enthalpy of overcrosslinking by decomposition, in the DSC measuring apparatus, of the residual peroxide of an EVA that has already undergone a prior crosslinking, in particular in a laminator. Comparison of the enthalpies of crosslinking between the two samples, the "fresh" and "laminated" samples, makes it possible to have an estimation of the level of crosslinking undergone by the sample in the laminator. When there is certainty of the formulation used in the EVA (same peroxide, same concentrations), the method can be applied relatively, by comparison of the enthalpies of overcrosslinking of samples laminated under different conditions, without having need to refer to the "fresh" EVA.

The method described in said article however has several drawbacks. In particular, this method is very indirect since it is based on the decomposition of the peroxide present as crosslinking initiating additive in the EVA, and not on the actual structure of EVA, which is a semicrystalline linear polymer before crosslinking, and a crosslinked network comprising crystalline zones after crosslinking. The method also requires the presence of residual peroxide, in the samples which have undergone a first crosslinking, and also the certainty that the only cause of disappearance of peroxide is the crosslinking operation in the laminator. It therefore does not function for EVAs no longer containing residual peroxide, and/or which has lost it via other phenomena (such as aging on storage or after lamination) than decomposition in the laminator, which involves prior knowledge of the thermal history of the sample. Now, this knowledge is not always acquired for the module manufacturer, who generally assumes that the EVA he receives is "fresh", i.e. has not undergone any decomposition of peroxide. During the determination of the degree of crosslinking via this method, the supposition must be made that the crosslinking reaction of the "fresh" EVA in the laminator, during the industrial crosslinking for the purpose of manufacturing a module, takes place in the same manner as the overcrosslinking in the DSC apparatus starting with an already-crosslinked EVA and residual peroxide. This supposition especially implies considering that the enthalpy of overcrosslinking measured by DSC for a sample crosslinked beforehand is a fraction of the total enthalpy measured by DSC when "fresh" EVA is crosslinked in the DSC apparatus. Now, this supposition is far from being indisputable. In point of fact, as has recently been demonstrated in the article entitled "*Assessment of Avrami, OZAWA and AVRAMI-OZAWA equations for determination of EVA crosslinking kinetics from DSC measurements*" from Bianchi, O., OLIVEIRA, R. V. B., FIORIO, R., DE N. MARTINS, J., ZATTERA, A. J. and CANTO, L. B., published in Polymer Testing 27 (2008), 722-729, the enthalpies of the crosslinking reaction of EVA with a peroxide, measured by DSC are not additive according to the amount of peroxide. Thus, for a given ramp rate, the enthalpy of the reaction with 2% peroxide is not twice as high as the same enthalpy with 1% peroxide, and the same goes for 4% peroxide relative to twice 2% peroxide. Furthermore, since the method is based on the decomposition of the peroxide present in the EVA, it requires total traceability in terms of origin, i.e. the EVA supplier, and of grade, and also a measurement of the enthalpy of decomposition of the "fresh" EVA for each formulation (grade, supplier). Even when it is used relatively, i.e. by comparing crosslinked samples with each other, the limits of the method appear when it is known that in order to use it in this manner, it is necessary to be sure that the EVA formulation of the compared samples is the same in terms of the type and initial concentration of peroxide. The method is not applicable for the analysis of samples originating from modules that have aged or originating from the terrain, since these modules may have lost, or may have undergone an age-induced reduction of, their residual peroxide content. The analysis technique is destructive and the analyzed sample is no longer available for repeatability measurements on the same sample. Finally, the crosslinking of EVA via means other than the use of peroxides, for instance radiation crosslinking, cannot be monitored via this method which does not reflect structural changes of the crosslinked EVA itself.

The article entitled "Characterization of mouthguard materials: thermal properties of commercialized products" is also known, published in August 2009 by Trenton E. Gould, Scott G. Piland, Junghwan Shin, Olivia McNair, Charles E. Hoyle, Sergei Nazarenko. This article discloses oral protectors, bulky objects used in a narrow temperature range (37° C.), mainly made of EVA whose vinyl acetate content is predetermined at about 18%. Part of this article mentions the use of the DSC method, but at no time is the EVA crosslinked. It is simply indicated that the EVAs of this study (relating to the thermomechanical properties of oral protectors consisting essentially of EVA) have the well-known thermal transitions of glass transition and melting (for the increasing-temperature ramps) and of crystallization (for the descending-temperature ramps).

In this study, the EVAs are never crosslinked and have a single content of vinyl acetate, and as such the characterization via the DSC method of these two aspects (crosslinking and content of vinyl acetate) is absolutely not studied, like the characterization via the DSC method of the fluidity or of the mass of the EVAs. Finally, this article discloses an EVA analysis based essentially on its melting zone and focuses only on the effect of the crystalline evolutions with time on the capacity of the material especially to absorb impacts.

Finally, the article entitled "DSC and TGA study of the transitions involved in the thermal treatment of binary mixtures of PE and EVA copolymer with a crosslinking agent" is known, published in 2006 by J. A. Reyes-Labarta, M. M. Olaya and A. Marcilla. This article lies in the field of polymer foams based on polyethylene or EVA. In this case, the EVAs are crosslinked, but the study relates only to the melting zone, the crystallization zone absolutely not being considered. Like the preceding article, this study does not exploit the data deriving from the DSC method for a monitoring/control of the vinyl acetate content or of the fluidity/molar masses of the polymers.

The aim of the invention is thus to overcome at least one of the drawbacks of the prior art. The invention is especially directed toward allowing a characterization of an EVA copolymer, by means of monitoring the degree of crosslinking without the drawbacks of the abovementioned methods. It also allows characterization of an EVA copolymer by means of a determination of the vinyl acetate content and/or of the molecular mass, and does so in a reliable and rapid manner that is easy to perform.

To this end, one subject of the invention is a process for characterizing a copolymer of ethylene and vinyl acetate (EVA) using a differential calorimetry analysis technique, characterized in that said process comprises the steps consisting in:

subjecting a sample of said EVA copolymer to a heat treatment, by temperature increases and decreases at constant rate, between a lower limit temperature of −80° C. and an upper limit temperature of 120° C., preferably between −70° C. and 100° C., to obtain a thermogram, on the thermogram obtained, detecting a temperature zone corresponding to a crystallization temperature zone (CR), characterizing the crystallization temperature zone (CR), presented in the form of a crystallization peak, said peak being determined by a maximum temperature (Tc) of said peak, a start temperature (Td) of said peak, a temperature of crossing (Tt) of two straight lines tangent to the descending slope of said peak and a shape factor (SF) of said peak, comparing said crystallization temperature zone (CR) with a corresponding crystallization temperature zone on reference thermograms, or with a corresponding temperature zone of crystallization temperatures on thermograms of other samples, as a function of the result of the comparison, determining one or more characteristic values of said sample of EVA copolymer, one of which is a degree of crosslinking of said sample and one is a vinyl acetate content of said sample.

When the thermogram of the sample to be characterized is compared with reference thermograms obtained for reference samples whose degree of crosslinking is known, the "level of crosslinking" corresponds to the value of the degree of crosslinking of the sample. On the other hand, when the thermogram of the sample to be characterized is compared relative to thermograms obtained for other samples whose degree of crosslinking is unknown, the "level of crosslinking" corresponds to the degree of crosslinking of the sample to be characterized relative to the other samples.

According to one possibility offered by the invention, it may be envisioned, on the thermogram obtained, in addition to detecting the temperature zone corresponding to the crystallization temperature zone CR, to detect a temperature zone corresponding to a transition temperature zone TV and/or a melting temperature zone FU.

In this hypothesis, the TV and FU zones are compared, like the CR zone, respectively to a glass transition zone and a melting temperature zone on reference thermograms or to a respectively corresponding zone on thermograms of other samples.

Advantageously, on the thermogram obtained, a glass transition temperature zone (TV) and a melting temperature zone (FU) are detected to be compared, respectively, with a corresponding glass transition temperature or melting temperature zone on reference thermograms or on thermograms of other samples; these zones (TV) and (FU) being, like the zone (CR), the subject of a characterization step.

It should be noted especially that the process of the invention illustrated in example 5 uses only the CR zone to perform the detection and comparison steps in order to determine a plurality of characteristics of the sample.

Thus, taking measurements at maximum temperatures not exceeding 120° C. and preferably not exceeding 100° C., implies that the EVA characterization process by DSC of the invention does not have the drawbacks of the prior art mentioned above, associated with the crosslinking taking place in the DSC machine. This novel process is not dependent on the formulation or the thermal history of the EVA samples.

Furthermore, since this process is based on structural changes brought about by crosslinking on the EVA, it may be applied to crosslinking modes other than that of the reaction brought about by peroxides, for instance irradiation crosslinking. This process is also simple, rapid and effective.

To take the measurements, use is made, for example, of a DSC machine which can heat up to at least 100° C. and which can cool down to at least −70° C., using a refrigeration system that allows stable functioning, such as a refrigerant bath containing refrigerant fluid. Such systems are proposed by DSC machine manufacturers, for instance TA INSTRUMENTS.

Such a machine comprises, for example, a supervision module that is arranged to control the steps of the characterization process according to the invention. This supervision module may be, for example, in the form of a processor programmed for this purpose. A set of computer program instructions allows the processor to perform various operations described hereinbelow in relation with the supervision module. Thus, the interpretation of the thermogram of the analyzed sample and its comparison with reference thermograms, or with other thermograms obtained or other samples, may be formed by means of a computer program comprising processor-run program code instructions, the processor possibly being located in the supervision module of the DSC machine.

Among the values of characteristics of the sample, determined after the comparison step, there is the level of crosslinking of the sample and also the vinyl acetate content present in said sample and advantageously at least one of the following values of characteristics: the fluidity and/or the molecular mass of said sample.

The heat treatment applied to the sample consists in forming heating/cooling thermal cycles, typically between −80° C. and 120° C., preferably between −70° C. and 100° C., on a sample of "fresh" or crosslinked EVA with a mass of between 2 and 15 mg and preferably between 6 and 12 mg. For the majority of the commercially available EVAs, the limits −70° C./+100° C. make it possible to reveal on the thermograms obtained 3 thermal phenomena. Thus, during the heating periods, a temperature zone appears corresponding to a zone of glass transition temperatures of the amorphous part of the copolymer. This zone appears at very low temperature, typically between −50 and −30° C. for the start of the transition. This zone is, for example, referenced TV in FIG. 1B described below with regard to example 1. Another temperature zone corresponding to a zone of melting temperatures of the crystalline part also appears during heating periods. This zone may cover a very wide zone which may overlap the glass transition temperature zone, but it has a peak whose apex is between 45 and 95° C. This zone is, for example, referenced FU in FIG. 1B. During the cooling periods, a third temperature zone appears. This zone corresponds to a zone of recrystallization temperatures of the crystalline part of the sample. This zone also has a peak that is between 75° C. and 20° C. It is, for example, referenced CR in FIG. 1B. The cooling period also reveals the temperature zone corresponding to the glass transition temperature zone of the amorphous part of the polymer (referenced TV). This zone is located in the same temperature zone as for the temperature increase, but it is less visible on the thermogram than during heating.

The characterization process consists in comparing the CR zone and optionally the two temperature zones TV and FU, detected on the thermogram of the analyzed sample, respectively at 3 corresponding zones on the reference thermograms. As a function of the result of the comparisons, the value(s) of the characteristic(s) of said sample of EVA copolymer are checked and/or determined.

The heat treatment applied to the sample to be analyzed is performed by repetition of a thermal cycle. In a first stage, the sample is cooled down to the lower limit temperature, for example −70° C. The temperature is then left to equilibrate, and the sample is then held at this temperature for at least a predetermined time which is about a few minutes, generally between 5 and 10 minutes. The sample is then heated up to the upper limit temperature, for example 100° C. The heating and cooling ramp rate is constant and chosen from values of between 5 and 20° C./min, and this rate is preferably set at 10° C./min. This operation, known as a cycle, is repeated at least once more and preferably twice more. Finally, the sample is cooled to a test end temperature. Typically, this test end temperature may be room temperature, for example 25° C.

The reference thermograms are preferably produced prior to the characterization process, by subjecting various known samples to the same heat treatment as that which is applied to the sample to be characterized, so as to determine three reference temperature zones: the glass transition temperature zone TV, the melting temperature zone FU and the crystallization temperature zone CR; and then in determining, in the zone chosen for exploitation of the data, one or more characteristic parameters of the selected transition. Such parameters may be, for example, the location of the chosen temperature zone in the temperature scale, the signal maximum or minimum, one or more changes in slope or points of inflection of the signal, crosses between straight lines tangent to the signal, a shape factor, an area under the curve (integral) between two temperatures corresponding to an energy value.

In all the cases, the transition chosen for exploiting the results is at least the temperature zone corresponding to the crystallization temperature zone, values or parameters such as the maximum temperature (Tc) of the crystallization peak, a peak start temperature (Td) obtained by crossing of the two straight lines tangent to the signal, a temperature of slope change after the crystallization peak maximum (Tt), or alternatively a shape factor (SF) of said peak may be associated with the transition. Exploitation of the temperature zone corresponding to the crystallization temperature zone detected with the process of the invention is particularly preferred and, regarding the exploitation of the crystallization temperature zone, the calculation of a shape factor (SF) of the peak is particularly preferred.

When the zone chosen for the exploitation of results is the glass transition zone, TV, values or parameters such as the glass transition temperature at the lowest point (Tgi), corresponding to the crossing of the straight lines tangent to the signal at the first inflection thereof, the glass transition temperature at the midpoint (Tgm) corresponding to the central point of inflection of the signal, the temperature corresponding to the crossing of the straight lines tangent to the signal at the last inflection thereof (Tgf) may be associated with the transition. When the transition chosen for exploiting the results is the melting zone (FU), values or parameters such as the minimum temperature (Tf) of the melting peak may be associated with the transition.

The known samples in particular have a known degree of crosslinking and/or a known composition, i.e. a known vinyl acetate content and a known molecular mass. Comparison of the three temperature zones TV, FU, CR detected on the thermogram of the sample to be analyzed relative to the corresponding zones of the reference thermograms then makes it possible to determine at least one of the following characteristics: the degree of crosslinking of the analyzed sample, the vinyl acetate content in the analyzed sample and also, if so desired, the fluidity or the molecular mass of said analyzed sample. According to a variant of the invention concerning the monitoring of crosslinking, the comparison may also be made between different samples with unknown degrees of crosslinking. Their relative level of crosslinking (classification) may also be formed with the process of the invention, without making use of a comparison with known or reference samples.

According to a variant of the invention, when only the CR zone will be exploited, the heating/cooling cycles may take place between two temperatures that are closer than the limit temperatures given above, provided that the target temperature zone is clearly encompassed, i.e. that it makes it possible to recover all the information necessary to perform reliable monitoring of the crosslinking or of the other mentioned characteristics (vinyl acetate content, fluidity, molecular mass). One of the ways of ensuring that the recovered information is reliable consists in checking the repeatability of the thermogram curves, and also of the values (for example peak temperatures) associated with the transitions and which make it possible to form the monitoring. Preferably, when, in order to save test time (duration of the measurements), the heating/cooling thermal cycle limits are close, a comparison of the results will be made with those obtained via the method with cycle limits at −70° C./100° C.

The Applicant has found, surprisingly, that the curves obtained after the successive cycles superpose extremely well with the exception of the EVA samples that are sparingly crosslinked or not crosslinked, for which the crystallization peak, especially, reflects a very slight but significant variation from one cycle to another. This is reflected, on the thermograms, by as many very close but discernible peaks as there are thermal cycles performed. Once the samples begin to be well crosslinked, this peak shift disappears and the superposition is then very good for the three temperature zones.

It is well known to those skilled in the art that the glass transition temperature (Tg) of polymers has a tendency to increase as a function of their degree of crosslinking. This was in fact observed on the thermograms obtained for analyzed EVA samples, in particular for EVA containing 33% commercial vinyl acetate, such as that used for the photovoltaic cell encapsulation applications. However, the increase of this temperature Tg is barely a few degrees, in the best of cases, which makes it possible to distinguish a well-crosslinked sample from a "fresh" (non-crosslinked) sample, but which makes the monitoring, for example, at different degrees of crosslinking, difficult. It is also well known to those skilled in the art that the crosslinking of EVA results in a change in its crystalline phase. This change may be reflected by a lower degree of crystallinity and/or by a reduction in size of the crystalline domains. It is generally accepted that the area under the curve (phase change energy) of a melting or crystallization peak as obtained in a DSC thermogram, reflects the degree of crystallinity of the sample and that the position of the peak (melting or crystallization peak temperature) depends on the degree of crystallinity and on the size of the crystalline domains.

It was nevertheless found by the Applicant, after various experiments, that the data arising from the crystallization zone are sufficient to characterize the crosslinking, the vinyl acetate content and optionally the fluidity and the molecular masses. Moreover, the use in the process of the invention of only crystallization data makes it possible to considerably reduce the time required for the characterization process.

It was found on the thermograms obtained for analyzed EVA samples of EVA containing 33% commercial vinyl acetate that the melting and recrystallization peak maximum temperatures decrease as a function of the degree of crosslinking. These two parameters may thus be used for the monitoring of the crosslinking according to the process described herein. On the other hand, the use of the phase change (melting or crystallization) energy, like the increase in Tg, appears to be unsuited for precise monitoring, for example of the crosslinking as a function of the lamination time or of the lamination temperature, due to its low amplitude of variation. Moreover, the thermograms obtained make it possible to observe that the most pronounced variations as a function of the degree of crosslinking take place in the temperature-descending ramp curves, in the crystallization temperature zone CR. Surprisingly, the Applicant has found that a person skilled in the art is unfamiliar with exploiting these DSC cooling curves for EVA, the studies being essentially performed on the basis of the temperature-increase thermograms.

On the thermograms obtained, the plot corresponding to the very first cooling of the sample, down to the lower limit temperature, referenced r1 in FIG. 1A described below with regard to example 1, does not make it possible to draw any exploitable results therefrom and may therefore be eliminated from the thermogram. Similarly, the first temperature rise, represented on the thermogram of FIG. 1A by the plot referenced c1, comprises a melting temperature zone, between 0 and 80° C., which is in the form of poorly repeatable peaks. Specifically, in this zone, the peaks associated with the first temperature rise do not superpose with the peaks of the plot associated with the second or the third temperature rise of the subsequent thermal cycles. In point of fact, the thermal transitions presented during the first temperature-increase ramp, which are poorly repeatable, are essentially linked to the thermal history of the sample and change as of the second temperature rise of the second thermal cycle. Specifically, from the second thermal cycle, the curves corresponding to the temperature rise are repeatable and superpose extremely well. Consequently, prior to the step of comparison of the characterization process, the plots r1 and c1 corresponding, respectively, to the very first cooling down to the lower limit temperature and to the very first temperature rise of the heat treatment are eliminated from the thermogram of the sample. Thus, prior conditioning of the samples, such as a conditioning time at defined temperatures and occasionally at controlled humidities, may be omitted.

As stated previously, exploitation of the crystallization temperature zone is preferred since it is sufficient in itself to successfully perform the characterization process according to the invention. The crystallization temperature zone CR is in the form of a crystallization peak for which the maximum or peak-start temperature, the maximum temperature of the signal (peak maximum) and the shape vary as a function of the degree of crosslinking. Consequently, prior to the step of comparison of a thermogram of an unknown sample with reference thermograms, an additional step of characterization of the crystallization peak consists in determining a maximum signal temperature Tc of the peak, a start temperature Td of the peak, a temperature of slope change after the crystallization peak maximum (Tt) or, alternatively, a shape factor SF of the peak.

The parameters (Tt) and (SF) reflect a very visible change in the shape of the crystallization peak, this change occurring after the peak maximum (toward lower temperatures). The crossing temperature (Tt) between two straight lines tangent to the thermogram and plotted on the descending slope of the crystallization peak may reflect this change of shape.

A second process for reflecting this change consists in determining a shape factor (SF) of the crystallization peak. The SF calculation consists, in a first stage, in determining the maximum temperature (Tc) of the crystallization peak. Temperature calculation limits [Tc; (Tc−X° C.)] encompassing the descending slope of the crystallization peak are then defined. They are defined, for example, by the maximum temperature (Tc) of the crystallization peak and by a low limit temperature (Tc−20° C.) equal to said maximum temperature (Tc) decreased by 20° C. A curve representing a ratio of temperature to heat flow (T/HF) as a function of the temperature is then plotted in the defined calculation limits. Next, on the curve thus plotted, a maximum value [max (T/HF)] of the ratio is determined and, finally, a shape factor SF value is calculated according to the following formula:

$$SF = \frac{\max(T/HF)}{Tc/\min(HF \text{ at } (TC-X \text{ °C.}))} *100;$$

in which min (HF at (Tc−X° C.)) represents a minimum value of the heat flow at the predefined low calculation limit temperature, for example Tc−20° C.

The parameter VC means a temperature variable (degrees Celsius) of between 10° C. and 50° C. and preferably between 15° C. and 30° C.

One and/or other of these parameters (Tt) or (SF) reflecting the shape of the crystallization peak is advantageously used to compare the shapes of the crystallization peaks between different samples or relative to reference thermograms.

The invention also relates to a process for controlling the quality of an EVA copolymer used in the manufacture of a photovoltaic module or in the manufacture of cables. This process consists in taking a sample with a mass of between 2 and 15 mg, and preferably between 6 and 12 mg, of said copolymer and subjecting said sample to the steps of the characterization process described above. The small need of material for the control and the fact that a particularly careful shape is not necessary for the collected sample mean that the sample can be easily recovered from film offcuts of real-size laminated modules. The collected sample will then be considered as having undergone the same treatment as the EVA film encapsulating the module. Alternatively, one or more sheets of film may be laminated under the same temperature profile and pressure profile conditions as a real module, with or without the other components (front face or front sheet, cells, back face or back sheet) of a module in what would be a sacrificial mini-module or mini-laminate for recovering the EVA film in order to collect a sample therefrom and subject it to the steps of the characterization/control process. This last way of proceeding also makes it possible, by collecting samples at different points on the crosslinked EVA film, to determine the crosslinking homogeneity on film sizes ranging from the mini-module to the film sizes of large-sized modules.

Finally, the invention relates to a process for controlling the resistance over time of an EVA copolymer used in the manufacture of a photovoltaic module, which consists in collecting, in a photovoltaic module that has aged, a sample with a mass of between 2 and 15 mg and preferably between 6 and 12 mg of said copolymer and subjecting said sample to the steps of the characterization process described above.

The characterization process thus makes it possible:
to eliminate the poorly repeatable effects linked to the thermal history of the sample (by especially eliminating the plot c1),
to ensure that the measurements taken are highly repeatable and reproducible,
to draw maximum sensitivity from the measurements relative to the level or degree of crosslinking of the EVA,
to render the exploitation of the data, arising from the DSC machine, automatic by means of an algorithm for quantifying the degree of crosslinking of a given sample.

The process allows a rapid, reliable and simple characterization. It uses little material and has no need to refer to other methods. It makes it possible to characterize EVAs crosslinked via various methods, not only by means of organic peroxides, but also by irradiation, for example. It also makes it possible to perform a post-manufacture control or analyses of products returning from the terrain, which is not possible with the DSC measurement process based on measuring the crosslinking enthalpies.

Figure 1B:
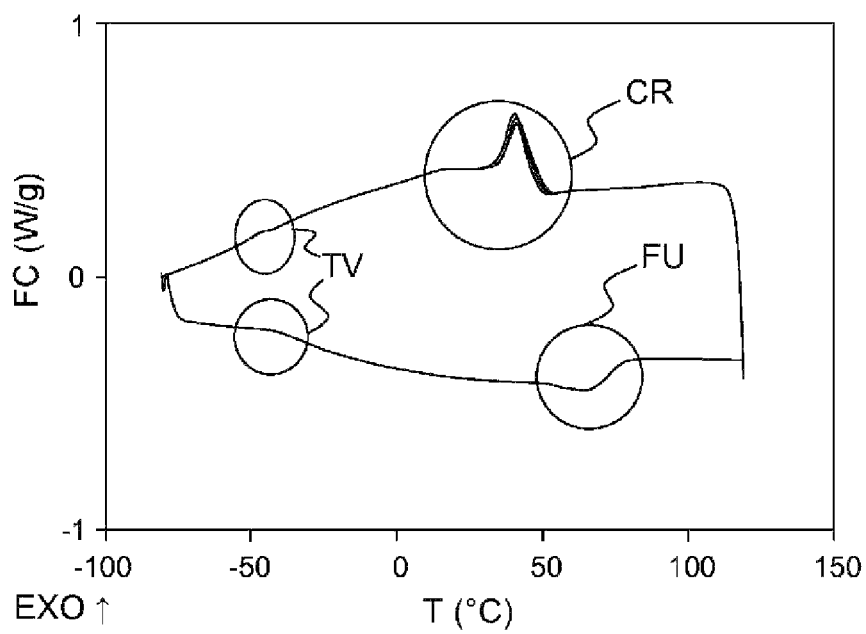
Figure 1C:
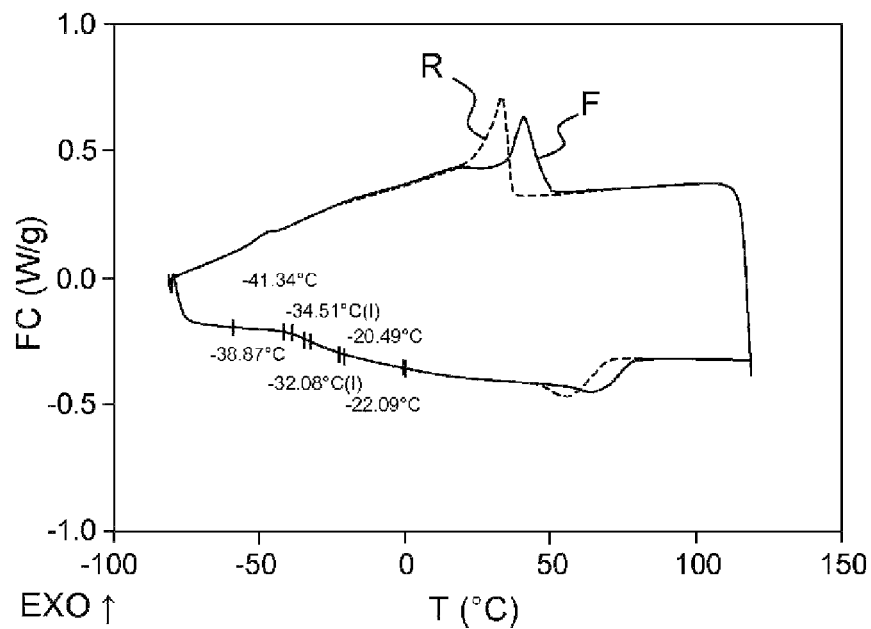
Figure 3:
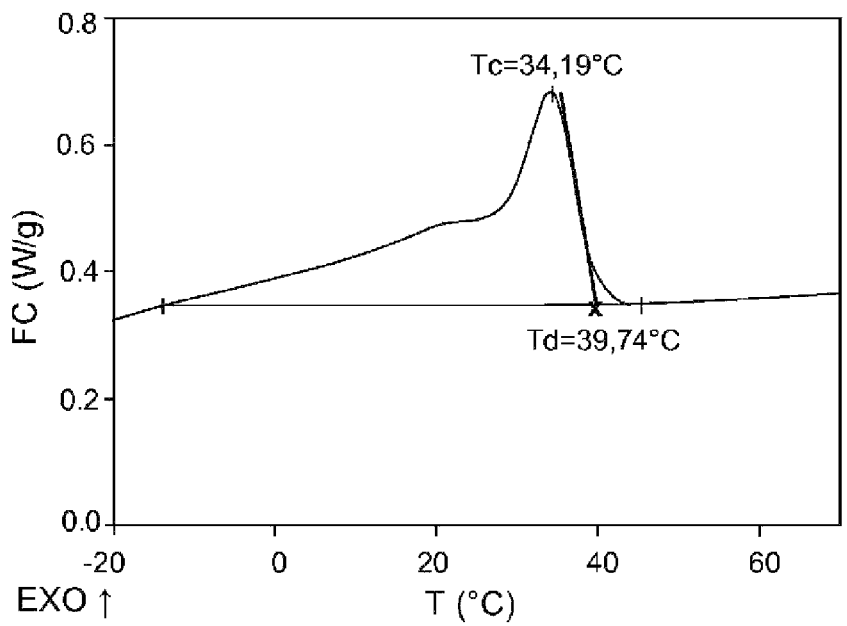
Figure 2:
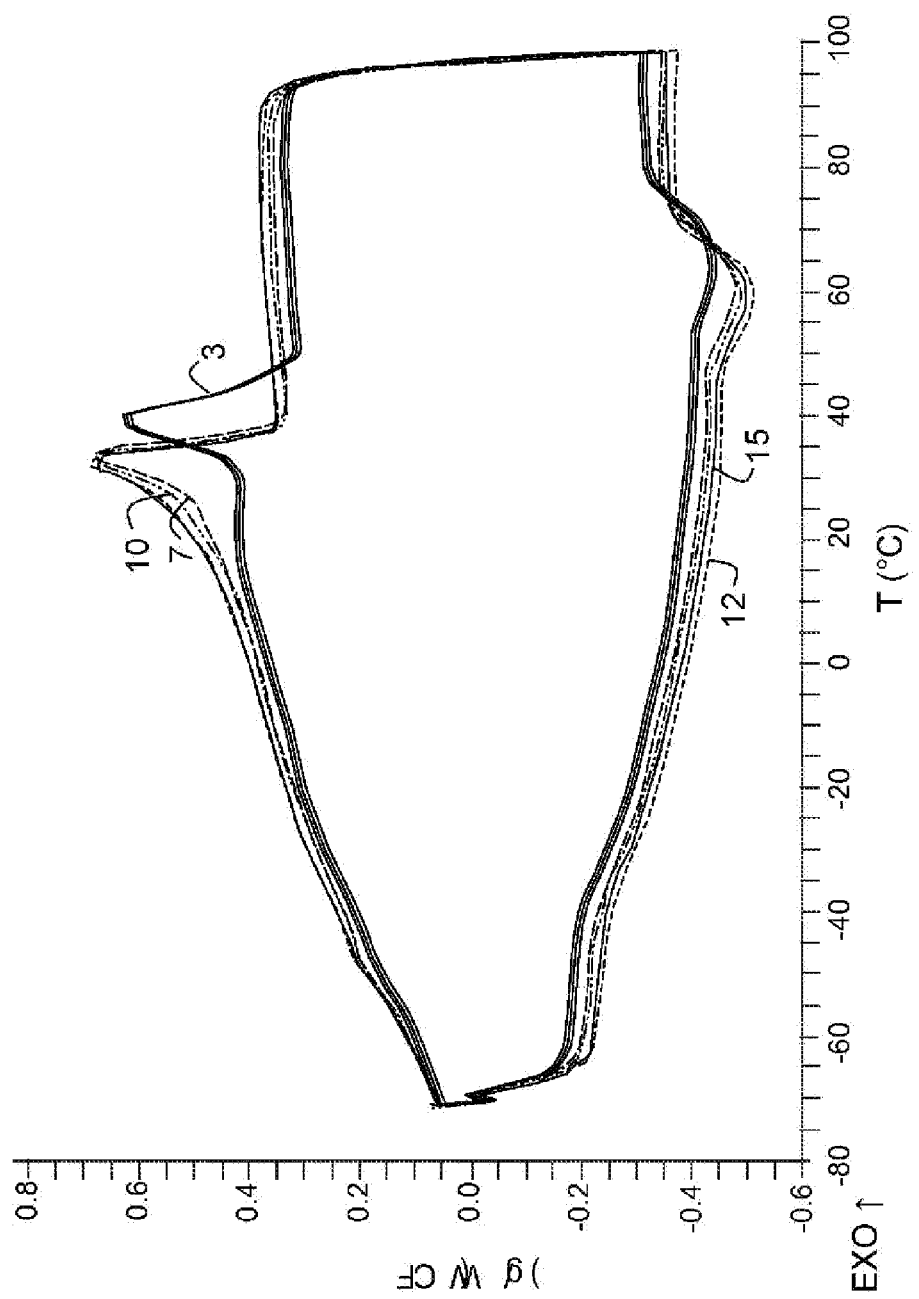
Figure 4:
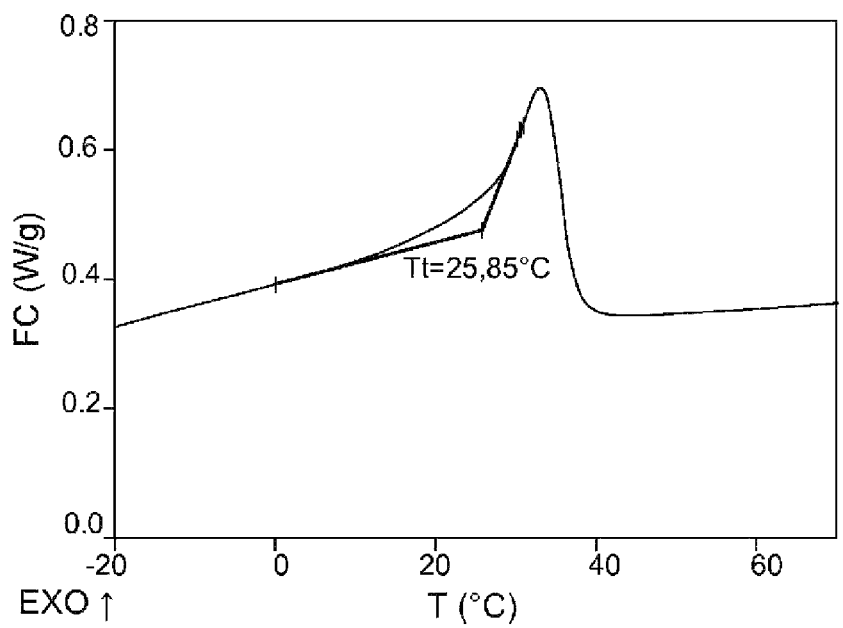
Figure 5A:
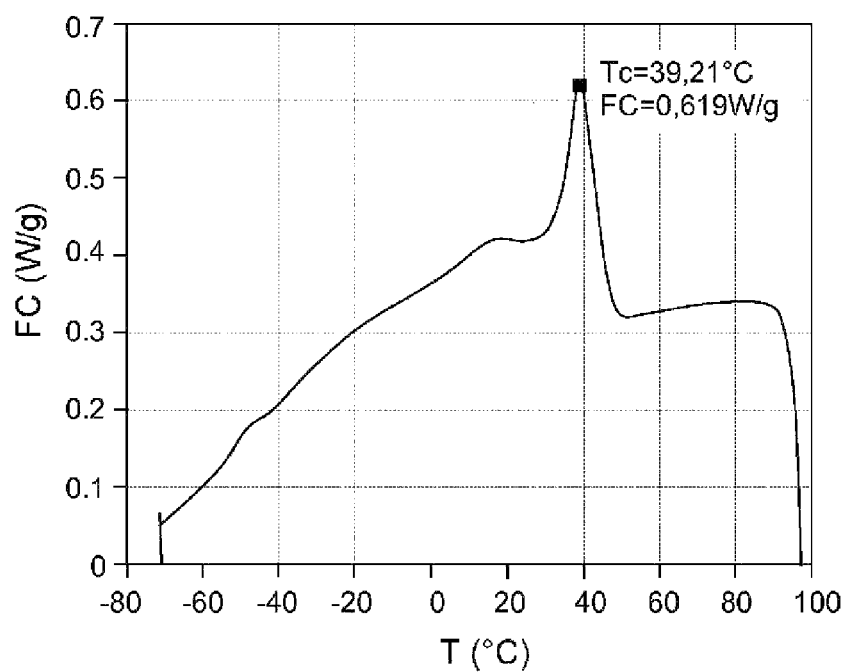
Figure 5B:
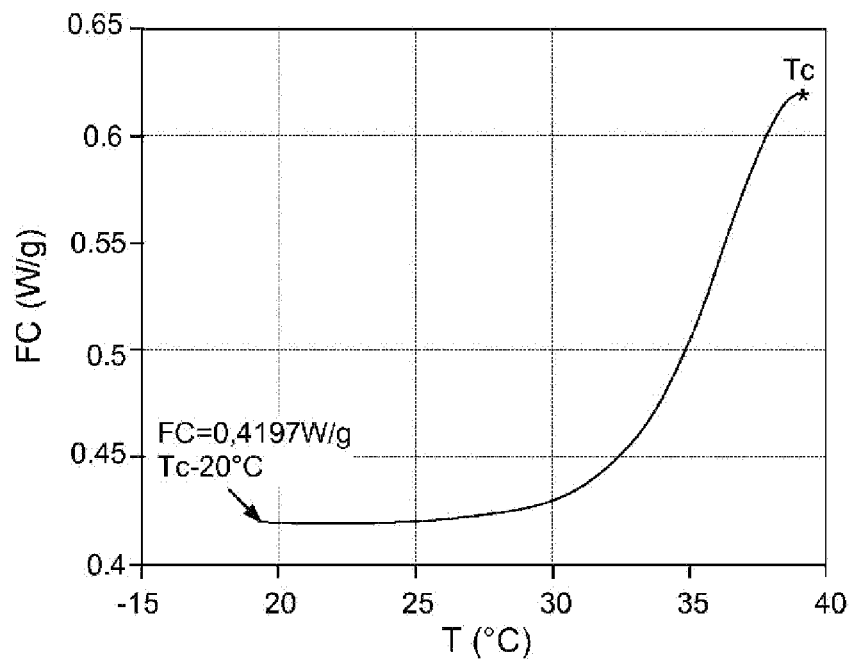
Figure 5C:
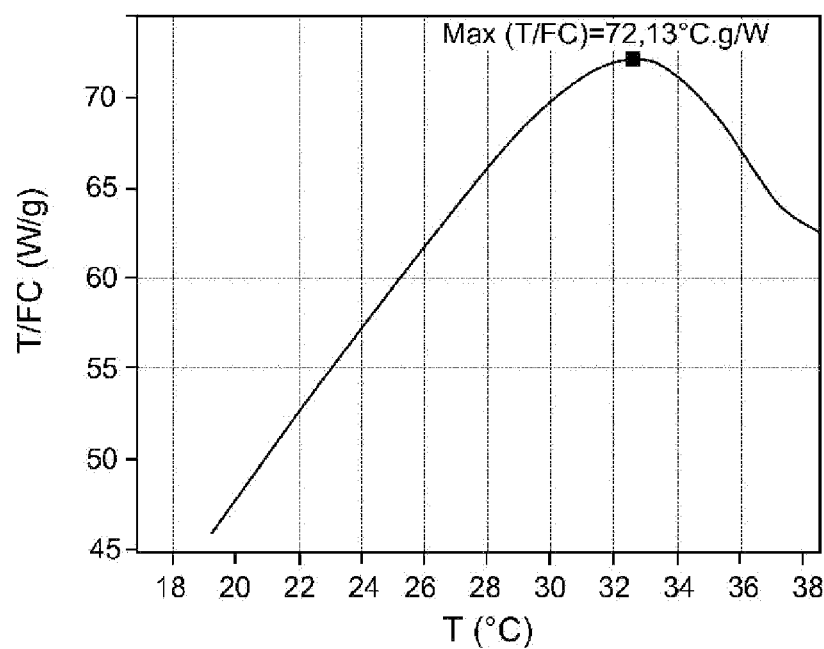
Figure 6:
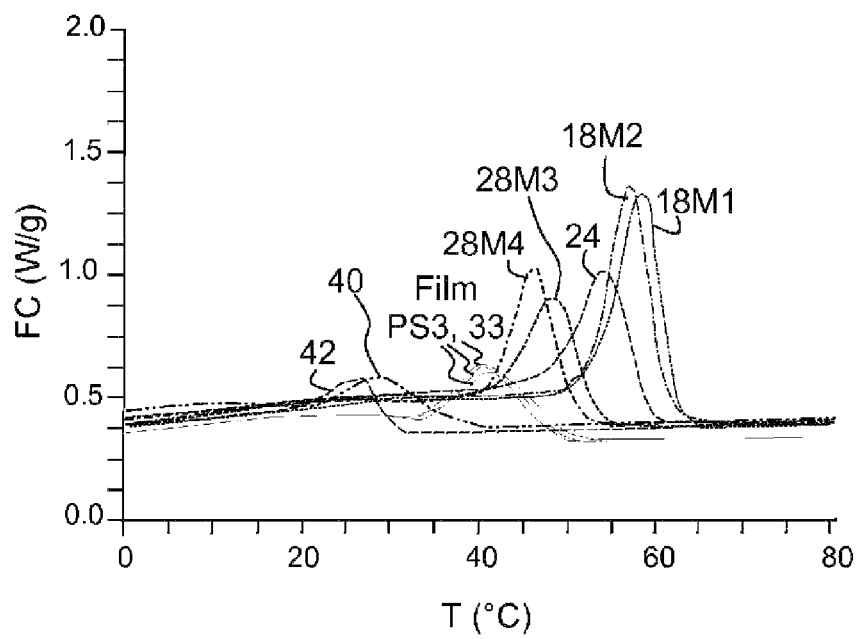
Figure 7:
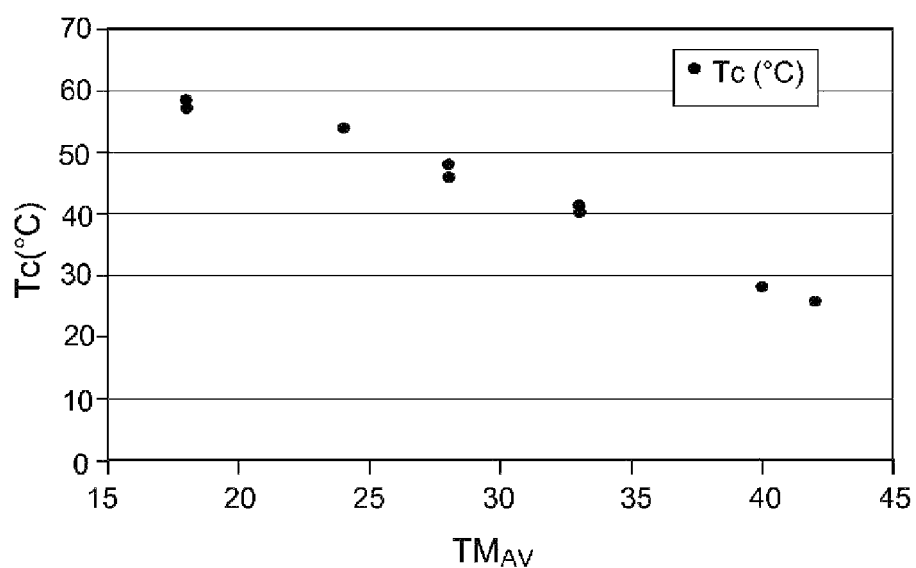
Figure 8:
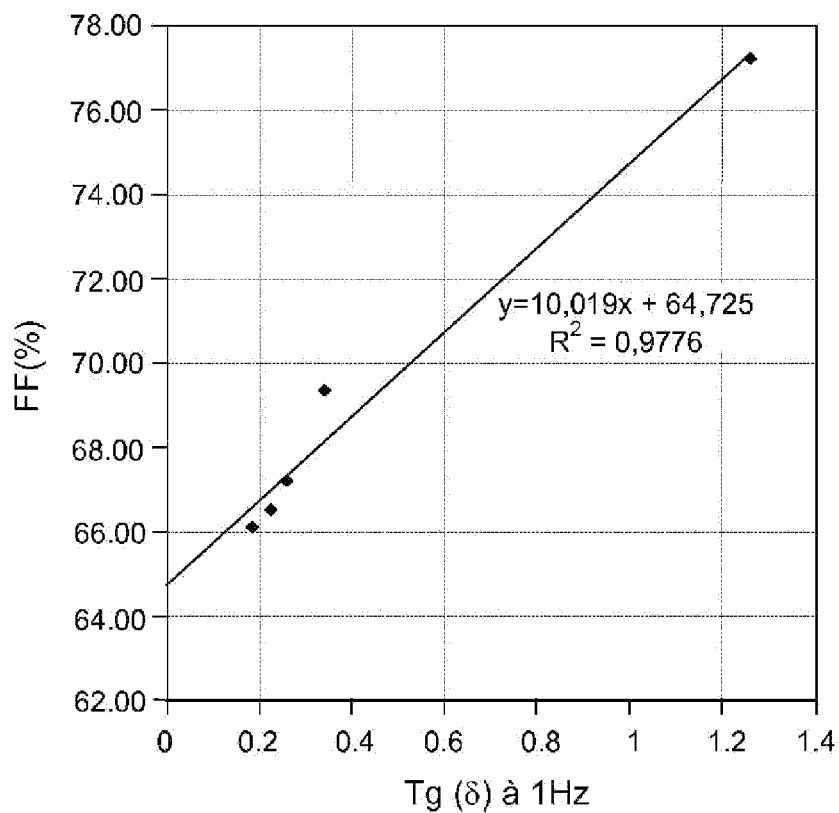
Figure 9:
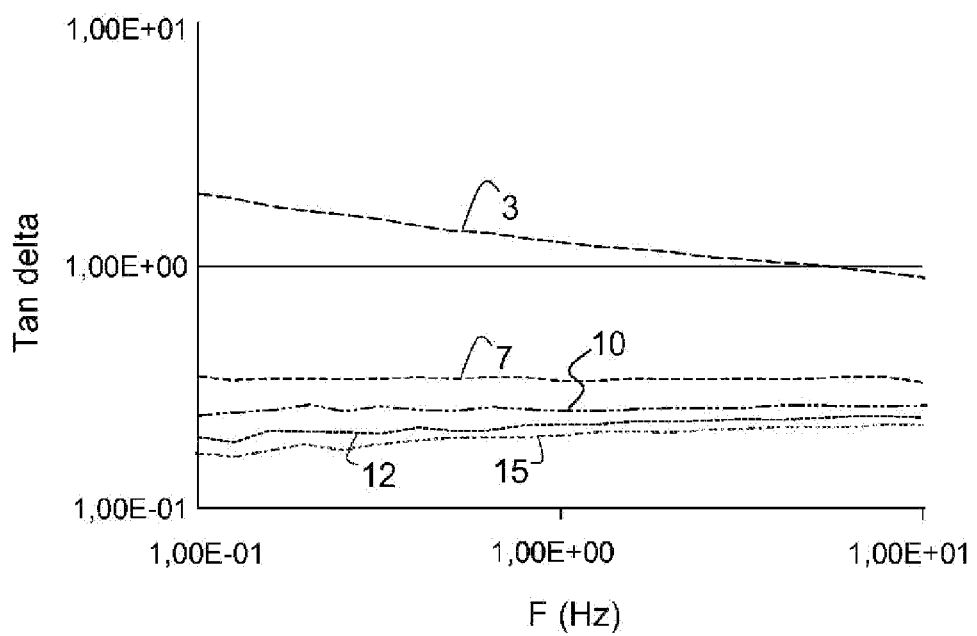

Other characteristics and advantages of the invention will emerge on reading the following examples given as nonlimiting illustrations, with reference to the attached drawings which represent:

FIGS. 1A to 1C, respectively a thermogram obtained for an EVA sample during the characterization process according to the invention, the same thermogram on which the plots corresponding to the unrepeatable thermal transitions have been deleted, and finally two thermograms, respectively, of a "fresh" sample and of the same sample after having undergone crosslinking, FIG. 2, thermograms obtained for an EVA sample after different lamination times, FIGS. 3 and 4, the enlarged crystallization temperature zone, respectively, of two thermograms obtained for two EVA samples crosslinked after different lamination times, FIGS. 5A to 5C, respectively, two curves representing an enlarged zone of the crystallization temperature zone of a thermogram and a curve representing a temperature to heat flow ratio as a function of the temperature, these three curves being used for a calculation of the shape factor of the crystallization peak, FIG. 6, various thermograms obtained for EVA samples of different compositions, FIG. 7, a curve representing the change in the crystallization peak temperature as a function of a mass content of vinyl acetate, FIG. 8, a curve of correlation between the results obtained with the process according to the invention and those obtained via the method for measuring the mechanical moduli by rheology, FIG. 9, curves of tangent delta as a function of the frequency, at a constant temperature of 100° C. obtained for an EVA sample after different lamination times, via the measuring method by rheology.

EXAMPLE 1

Monitoring of Crosslinking by Treatment in the DSC Machine

A first EVA sample, containing 33% by weight of vinyl acetate, was analyzed according to the characterization process according to the invention. In a first stage, this sample was analyzed "fresh", i.e. without prior crosslinking, on receiving it from a manufacturer of EVA films for photovoltaic modules. In a second stage, this same sample was analyzed after crosslinking performed directly in the DSC machine, by heat treatment at 150° C. for 30 minutes.

To do this, 9.6 mg of the EVA sample containing 33% vinyl acetate are placed in a crimped aluminum capsule and introduced into the measuring chamber of a DSC machine. The weight of the capsule containing the sample is determined by difference between the full crimped capsule and the same capsule with its lid, weighed before introducing the sample. All the weights are noted. Another crimped capsule, not containing a sample, also made of aluminum, is also introduced into the measuring chamber, as a reference cell. The DSC machine used is a Q10 machine from the company TA INSTRUMENTS, equipped with an automatic thermal-fluid cooling system, model RCS 90, making it possible to descend to about −80° C. Throughout the measurement, the DSC machine controls an automatic flow of flushing nitrogen in the measuring chamber, so as to avoid oxidation reactions. This nitrogen flush is performed with a flow rate of 50 ml per minute.

To perform the characterization, the EVA sample to be analyzed is subjected to the following heat treatment: The sample is cooled to −80° C. at a rate of 10° C./minute. After equilibrating the temperature, the sample is maintained at this temperature for 10 minutes. The sample is then heated up to 120° C., at a rate of 10° C./minute. This thermal cycle is then repeated twice. Finally, the sample is cooled to 25° C., at a rate of 10° C./minute. FIG. 1A represents the thermogram obtained after this heat treatment. This thermogram more particularly represents the mass flow of heat, in watts/gram (W/g), as a function of the temperature in ° C.

On this thermogram, the three temperature zones corresponding, respectively, to a glass transition temperature zone TV, a melting temperature zone FU and a crystallization temperature zone CR are distinguished. These zones are surrounded in FIG. 1B.

FIG. 1B illustrates the same thermogram, after the plots r1 and c1 of the thermogram of FIG. 1A, corresponding to the unrepeatable thermal transitions, linked to the thermal history of the sample, have been eliminated. The resulting thermogram comprises the curves of 2 temperature rises which superpose perfectly, and of 3 temperature decreases, the last of which stops at room temperature, which also superpose perfectly. On this thermogram, the temperature zone TV corresponding to the glass transition temperature zone at about −40° C., and also the temperature zone FU corresponding to the melting temperature zone whose peak appears at about 65° C., are detected during the heating. During the cooling, the temperature zone CR corresponding to the crystallization temperature zone whose peak is located at about 40° C. is detected. The glass transition zone TV is again perceptible on cooling, but is much less well defined than during heating.

The sample thus analyzed is then heated to a temperature of 150° C. and maintained at this temperature for 30 minutes under a flush of nitrogen. This thermal treatment at 150° C. for 30 minutes has the consequence of bringing about crosslinking of the EVA sample. After this crosslinking, the sample is subjected to the same heat treatment applied to the fresh EVA and described above in this example, for the purpose of obtaining a thermogram. By comparing the thermogram obtained, referenced R in FIG. 1C, with that of the fresh sample, referenced F in FIG. 1C, it is observed that the effect of the heat treatment at 150° C. for 30 minutes and which brought about crosslinking of the sample is barely perceptible in the glass transition temperature zone TV. Specifically, in this zone, a slight increase in the glass transition temperature Tg is observed after crosslinking. On the other hand, this effect is clearly visible in the melting temperature zone FU since a shift towards low temperatures of the melting peak and an appreciable decrease in the melting peak minimum with crosslinking are noted. This effect is above all visible in the crystallization temperature zone CR, since a very marked decrease in the maximum temperature Tc of the peak with crosslinking is noted, but also a marked change in the shape of the peak. Finally, the capsule containing the sample is weighed again after all the measurements and treatment. Its mass has not changed within the sensitivity limit of a balance to within a tenth of a milligram.

EXAMPLE 2

Determination of the Relative Level or Degree of Crosslinking of Samples Laminated Under Industrial Conditions Various EVA samples containing 33% vinyl acetate, laminated at different times, were analyzed according to the characterization process. The samples are laminated in an industrial laminator for photovoltaic panels. Since the lamination times are different, the samples all have different degrees of crosslinking.

For this, EVA sheets, of photovoltaic grade containing 33% vinyl acetate from the company ETIMEX, are arranged in a stack comprising a glass plate, a sheet of nonstick plastic (Teflon®), the sheet of EVA to be crosslinked, a new sheet of nonstick plastic and 2 sheets of a nonconforming EVA ("old"), serving as a damping cushion. This stack, in mini-module format (16×16 cm), is then placed in a module laminator with two stacked chambers, from the company 3S, model S1815E.

The lamination is performed in the following manner: the laminator temperature is raised to a nominal temperature of 145° C. and the stack of layers is then introduced into the lower chamber of the laminator. The laminator is then closed and its two chambers are placed under vacuum (about 1 mbar). The temperature is maintained at 145° C. for 5 minutes, without the laminate being in direct contact with the heating plate of the laminator. This is known as phase 1, the degassing phase, during which the EVA approaches its melting point and the temperature of the laminate becomes homogenized, at about 70° C. The upper chamber is then returned to atmospheric pressure, and the laminate is placed directly in contact with the heating plate and maintained in this configuration for the chosen lamination time. This is known as phase 2, the actual lamination phase, during which the temperature of the laminate rises rapidly to the nominal value of 145° C. plus or minus 3 degrees and a pressure of about 1 bar is applied via the lap separating the upper chamber from the lower chamber (reminder: the lower chamber is under vacuum and the upper chamber is at atmospheric pressure during this phase). At the end of this second phase, the pressures of the two chambers are equilibrated and the laminate is ready to be removed from the laminator. Finally, the laminate is removed while hot from the laminator and then cooled to room temperature. It is then disassembled and the EVA sheet thus crosslinked is recovered to be used in the characterization process according to the invention.

Lamination times (actual lamination phase 2) of 3, 7, 10, 12 and 15 minutes are selected for the crosslinking of just as many EVA sheets according to the above protocol.

Samples of between 8 and 12 mg of the EVA sheets thus crosslinked are prepared for the DSC measurement, according to the process of example 1.

A heat treatment similar to that of example 1 is applied to each of the samples in order to obtain thermograms for each of them. This heat treatment consists in:
1) decreasing as rapidly as possible to −70° C.,
2) equilibrating the temperature at −70° C.,
3) maintaining at −70° C. for 5 minutes,
4) rising to 100° C. at a rate of 10° C./minute,
5) decreasing to −70° C. at a rate of 10° C./minute,
6) repeating steps 2 to 5, twice,
7) returning to 25° C. at a rate of 10° C./minute.

FIG. 2 shows all of the DSC curves for the 5 samples at different lamination times, after deletion of the recordings corresponding to the first rapid decrease to −70° C., the last rise to 25° C. and the first rise to 120° C. of the first thermal cycle (deletion of the unrepeatable peaks linked to the thermal history of the sample as explained above). In this figure, the curves are referenced 3, 7, 10, 12, and 15, which references correspond, respectively, to the lamination times of the corresponding samples.

These DSC plots correspond, for each sample, to 2 increase passages and 3 decrease passages. It may be observed, as for example 1, that the curves are very repeatable, since perfectly superposed. The least crosslinked sample, corresponding to the lamination time of 3 minutes (curve referenced 3) still shows slightly poorer repetitivity. Specifically, the 3 decrease passages are discernible (the crystallization peaks are slightly shifted). This slight repetitivity defect disappears once the crosslinking time advances, and the difference between the crosslinking times is greater than the difference in repetitivity observed only for the first time of 3 minutes. Observation of these curves shows the distinctive traits of example 1, i.e. there is little resolution in the glass transition temperature zone, a decrease in the minimum temperature Tf of the melting peak, a decrease in the maximum temperature Tc of the crystallization peak and a marked change in the shape of this crystallization peak.

The thermograms thus obtained for samples having different degrees of crosslinking may then serve as reference thermograms during the characterization of an EVA sample, in order to know its degree of crosslinking. Comparison of the thermograms of these samples with each other also makes it possible to classify the samples from the least crosslinked to the most crosslinked; treatment of the curves with the parameters mentioned above such as Tc, Td, Tt, SF, makes it possible to assign a numerical value to each sample, this value reflecting its level of crosslinking relative to the other samples. In this example, the vinyl acetate content of the analyzed samples is constant and equal to 33% by weight and the molecular mass is also identical for all the samples, since they are obtained from the same sheet of EVA.

Table I shows the glass transition temperature values Tg obtained from the DSC plots, as a function of the lamination time $t_{lam}$.

TABLE I

| $t_{lam}$ (min) | Tg (° C.) |
|---|---|
| 3 | −40.4 |
| 7 | −39.3 |
| 10 | −39.3 |
| 12 | −39.0 |
| 15 | −37.9 |

The glass transition temperature values Tg obtained correspond to the first point of inflection, Tgi (determined via the well-known method of crossing of 2 tangents to the signal) of the glass transition temperature zone TV. The glass transition temperature values Tg of table I are obtained using the data processing computer program of the TA INSTRUMENTS machine, the computer program known as "Universal Analysis" or "WinUA". To do this, it is necessary to give the computer program two bottom and top limit temperatures, encompassing all of the glass transition zone, TV. When the top and bottom limit temperatures of the temperature zone TV vary, for example when the bottom limit is set at −55° C. but the top limit is taken at −20° C., then −10° C., then 0° C., then 10° C., then 20° C., then the calculation computer program can give slightly different glass transition temperature values Tg. In this example, a mean of these various values (5 pairs of limit temperatures) was calculated. The procedure is easily programmable for the purpose of making it automatic. From the values of the glass transition temperature Tg thus obtained, if a curve of this temperature Tg is plotted as a function of the lamination time, an increasing tendency may be revealed with a coefficient of correlation of greater than 0.97 for a straight line. However, the values, even between the extreme lamination times (i.e. between 3 and 15 minutes) are quite close since they are within a temperature range of barely 2.5° C. The glass transition zone Tg thus makes it possible to significantly differentiate a well-crosslinked sample (15 minutes of lamination) of another that is very sparingly crosslinked (3 minutes), but precise and reliable monitoring as a manufacturing control method, as a function of the lamination time is more intricate.

Table II shows the temperature values Tf of the melting peak minima as a function of the lamination time $t_{lam}$.

TABLE II

| $t_{lam}$ (min) | Tf (° C.) |
|---|---|
| 3 | 65.8 |
| 7 | 62.4 |
| 10 | 61.5 |
| 12 | 60.8 |
| 15 | 60.6 |

These values may be obtained, for example, using a data processing computer program for the machine, for example the computer program "Universal Analysis" (WinUA), with defined top and bottom integration limits encompassing the melting peak, for example between 10 and 90° C. It may be observed that the total temperature difference between these two extremes (lamination time of 3 and 15 minutes) is virtually doubled compared with the total difference in glass transition temperature Tg. These different minimum temperature values of the melting peaks reflect significant differences in the level of crosslinking of the samples and make it possible to classify them as a function of the progress of the crosslinking reaction. If, in addition, the crosslinking node density of these samples is determined via a direct method, these temperatures may be converted directly into degrees of crosslinking.

Table III shows the maximum temperature values Tc of the crystallization peaks, and also the start temperatures Td for said peak. The start temperature Td is obtained by plotting two straight lines tangent to the DSC plot on cooling, i.e. a tangent to the base line, before the start of the peak, and a tangent to the rising slope of the peak associated with the start of crystallization. The crossing of the two tangents makes it possible to obtain a value of Td. This determination of the start temperature is illustrated in FIG. 3. These temperatures Tc and Td are calculated, for example, using the "Universal Analysis" computer program mentioned above. Top and bottom integration limits encompassing the crystallization peak are also defined and indicated in Table III.

TABLE III

| $t_{lam}$ (min) | Integration limits (° C.) | | Tc (° C.) | Td (° C.) |
|---|---|---|---|---|
| 3 | −14.0 | 55 | 39.1 | 46.8 |
| 7 | −14.7 | 45 | 33.6 | 38.4 |
| 10 | −13.9 | 45 | 32.9 | 37.3 |
| 12 | −13.9 | 45 | 32.6 | 37.0 |
| 15 | −13.5 | 45 | 32.2 | 36.7 |

In this table, it is seen that the peak apex Tc and start Td temperatures follow a clear tendency as a function of the lamination time with a difference between the extreme times that is even more pronounced than for the minimum temperature of the melting peaks Tf.

To associate a value to the shape of the crystallization peak, two processes were developed and applied.

The first consists in determining a crossing point Tt of two straight lines tangent to the thermogram and plotted on the descending slope of the crystallization peak, as illustrated in FIG. 4. This determination of the crossing temperature Tt of the two tangents may be made using the same computer program as previously, for example the "Universal Analysis" computer program. Table IV below shows the variation of this crossing temperature Tt as a function of the lamination time. This crossing temperature Tt, like the temperatures Tc of the crystallization peak maximum and the crystallization start temperature Td, follow a clear tendency as a function of the lamination time. The results make it possible to assert that the most pronounced changes in crosslinking take place between 3 and 7 minutes of lamination. Clearly a sample at 3 minutes of lamination is very sparingly crosslinked: the shape of the crystallization peak is very similar to that of a "fresh" sample, and the crystallization peaks of the 3 thermal cycles in descent do not superpose perfectly. The crosslinking continues to progress, but to a lesser extent from a lamination time of 7 minutes, and above all from a lamination time of 10 minutes.

TABLE IV

| $t_{lam}$ (min) | Tt (° C.) |
|---|---|
| 3 | 32.7 |
| 7 | 27.5 |
| 10 | 25.7 |
| 12 | 24.6 |
| 15 | 23.6 |

The second process for attributing a numerical value to the shape of the crystallization peak is the method making use of the determination of a shape factor SF. This method, not included in the "Universal Analysis" processing computer program was developed to take better account of all of the shape of the crystallization peak from the peak maximum temperature to temperatures where all the curves recover the same shape of a descending straight line.

Let us take, for example, the case of sample 3, after 3 minutes of lamination; the data processing for the crystallization peak and the steps in which the calculation of the shape factor is involved are the following: the crystallization temperature value Tc corresponding to the crystallization peak maximum is first determined. The determination of this value Tc is illustrated in FIG. 5A which represents an enlarged zone of the crystallization peak. Tc=39.21° C. in the example (see FIG. 5A). The part of the curve between the top calculation limit, Tc, and bottom calculation limit, T=Tc−20° C., encompassing the descending part of the crystallization peak, is then recovered. This curve part is represented in enlarged form in FIG. 5B. In the determined calculation limits, a curve representing the temperature to heat flow ratio (T/HF) as a function of the temperature is plotted. This curve is illustrated in FIG. 5C. On the curve thus plotted, a maximum value [max(T/HF)] of the ratio is determined. This value is equal to 72.13° C.g/W in the example and as is readable on the curve of FIG. 5C. Finally, a shape factor SF value is calculated according to the following formula:

$$SF = \frac{\max(T/HF)}{Tc/\min(HF \text{ at } (Tc\text{-}20 \text{ °C.}))} * 100;$$

in which min (HF at (Tc−20° C.)) represents a minimum value of the heat flow at the bottom calculation limit temperature (Tc−20° C.). This value is equal to 0.4197 W/g in the example and as is readable in FIG. 5B.

In this example, the shape factor SF of the crystallization peak of the sample crosslinked with a lamination time of 3 minutes is thus equal to:

$$SF=(72.13/(39.21/0.4197))*100=77.20\%$$

Advantageously, the method for determining the shape factor was automated by programming an executable. This computer program is executed by a processor which may be inserted, for example, into a supervision module of the DSC measuring machine. It makes it possible especially to process a DSC file, to produce all of the graphs, to determine the glass transition Tg, melting Tf, crystallization Tc, crystallization-start Td and crossing Tt temperatures of the tangent straight lines on the descending slope of the crystallization peak and to calculate the shape factor SF. As for the values of the temperatures Tf, the temperatures Tc, Td, Tt and the shape factor SF reflect significant differences in the level of crosslinking of the samples and make it possible to classify them as a function of the progress of the crosslinking reaction. If, in addition, the crosslinking node density of these samples is determined via a direct method, these temperatures may be converted directly into degrees of crosslinking.

EXAMPLE 3

Determination of the Vinyl Acetate Content of an EVA Sample

According to another aspect of the invention, the DSC method of the invention may also be applied to the determination of the vinyl acetate content of an EVA sample. FIG. 6 shows a magnification of the CR zone of the crystallization peak for EVA samples comprising different vinyl acetate contents and different fluidities, i.e. with different molecular masses.

In this figure, the curves are referenced by the numbers 18, 24, 28, 33, 40, 42, corresponding to the mass contents of vinyl acetate in the analyzed EVA samples.

Two curves 18 and two curves 28 are also differentiated by the characters M1, M2, M3 and M4 since they correspond to samples having an identical vinyl acetate content of 18% and 28%, respectively, but having a different fluidity and molecular mass, respectively M1, M2 and M3, M4.

It appears clearly that the temperature Tc of the crystallization peak maximum decreases as a function of the vinyl acetate content. It is thus possible to determine the vinyl acetate content of an unknown EVA sample by comparison with the reference thermograms corresponding to samples of known content. Thus, the insertion of the DSC curves for the non-crosslinked sample of example 1 of EVA containing 33% vinyl acetate, curves referenced 33, is clearly done in the range between an EVA containing 28% and an EVA containing 40% vinyl acetate, as shown in FIG. 6.

Moreover, FIG. 7 shows the change in the temperature Tc of the crystallization peak maximum as a function of the mass content $TM_{VA}$ of vinyl acetate. It appears clearly that the uncertainty linked to the fact that the non-crosslinked samples do not superpose perfectly is lower than the differences in temperature Tc of the peak maximum that may be attributed to the vinyl acetate content. Furthermore, the curve shows a portion that is quite linear between 24% and 42% by mass of vinyl acetate, which makes it possible to obtain via the DSC method the vinyl acetate content of an unknown sample with very good precision. Thus, starting from the crystallization temperatures, the correlation predicts a mass content of between 31.1% and 31.9% for the sample of example 1, the theoretical nominal content of which is 33%.

DSC thus makes it possible to determine with good precision the vinyl acetate content of an EVA irrespective of its fluidity, and vice versa. It also makes it possible to work backwards to the fluidity and thus to determine the molecular mass.

EXAMPLE 4

Comparison of the DSC Method of the Invention with a Known Method for Monitoring Crosslinking Consisting in Measuring Mechanical Moduli by Rheology Samples of laminated EVA sheets of example 2 were prepared and subjected to dynamic measurements of the shear modulus as a function of the oscillation frequency, at a constant temperature of 100° C., in an Anton Paar Physica MCR 301 machine, in plate/plate mode, with the following spindle references: MCR 301 SN80102900; FW3.22; Slot9; Adj20d. Circular samples were cut out of laminated EVA sheets as described in example 2, using a sample punch to the dimensions of the spindle used. The deformation was kept constant at 0.1%, which remains within the linear viscoelasticity zone. FIG. 9 shows curves, referenced 3, 7, 10, 12 and 15, of tangent delta=G"/G' as a function of the oscillation frequency at 100° C. for the samples crosslinked after lamination times, respectively, of 3, 7, 10, 12 and 15 minutes. These measurements clearly show that the sample at a lamination time of 3 minutes is not crosslinked enough, since its viscoelastic behavior as a function of the frequency is that of a viscoelastic liquid at low frequency as explained below. On the other hand, for the samples at and above a lamination time of 7 minutes, such viscoelastic liquid behavior could not be demonstrated in the explored frequency range. In this example, a difficulty in analyzing samples at and above 10 minutes of lamination was demonstrated, which, due to their crosslinking, become sufficiently solid for the rheometer under the conditions used, which gives rise to slippage problems reflected by very noisy curves at low frequencies. As a result, the analysis is limited to a frequency zone not going any lower than 0.1 Hz and to the tangent delta curves, defined as the ratio of the dynamic moduli G" (imaginary or viscous part of the complex shear modulus) and G' (real or elastic part).

It is clearly seen in FIG. 9 that the sample at a lamination time of 3 minutes (curve 3) crosses the tangent delta=1 value and that the tangent delta continues to increase at low frequencies. This behavior is typical of a viscoelastic liquid material since, from a tangent delta=1 and for values higher than 1, the viscous modulus, G", is greater than the elastic modulus G'. On the other hand, for the other lamination times (7, 10, 12 and 15 minutes), the corresponding curves 7, 10, 12 and 15 of tangent delta, which reflect the proportion of liquid (viscous) behavior relative to the solid (elastic) behavior are markedly lower and have virtually no slope. This suggests that even at very low frequencies (not accessible in these measurements) the tangent delta curve will not arrive at the value of 1, and even less so exceed it. It is also seen that the greatest difference arises between lamination times of 3 and 7 minutes and that from 7 minutes the differences become attenuated, since the samples are sufficiently rendered elastic solids by the crosslinking. This is exactly the same type of behavior that is demonstrated by the DSC technique, according to the characterization process performed in examples 1 to 3. FIG. 8 shows the change in the shape factor SF of the crystallization peak obtained via the DSC method of the invention, as a function of the tangent delta value obtained, at 1 Hz, via the rheology measurement method. It is seen in this figure that the coefficient of correlation is very good and close to 0.98. This good agreement reflects the same tendency between the data obtained via the DSC treatment described above and rheological tests.

The process according to the invention thus makes it possible to determine the value of at least one characteristic, namely the degree or level of crosslinking of an EVA sample, in a simple, reliable, rapid and precise manner. The results obtained are comparable to those obtained via standard methods that are much more complicated to implement.

The process also makes it possible to determine the value of a second and of a third characteristic, namely, respectively, the vinyl acetate content and the molecular mass of the EVA sample.

EXAMPLE 5

Use of the Method for the Quality Control of Photovoltaic Modules Just after Manufacture In this example, the DSC machine of the preceding examples is used. Samples of EVA encapsulator are taken from real photovoltaic modules consisting of a laminate of layers, namely: a transparent front face made of glass or of transparent polymer, one or more front layers of encapsulator, a skeleton of photovoltaic cells soldered together with electricity-conducting connectors, one or more rear face layers of encapsulator and a rear face of polymer, glass or polymer/glass fiber composite. In all the cases, the EVA is a photovoltaic grade EVA containing 33% by weight of vinyl acetate, described in example 2. The laminations were formed in the laminator of example 2. The lamination programs used were variable according to the configuration of the module (size, types of front face and rear face), but in all the cases, suitable crosslinking conditions were sought with nominal temperatures of at least 145° C. and actual lamination times, after the degassing step, of at least 10 minutes, unless otherwise indicated (shortened lamination). In this example, only the crystallization zone (CR) is exploited, and starting from the DSC thermograms which may be obtained by following the heating/cooling steps of the preceding examples or, in an optimized manner, by using the following reduced program:

1) equilibration of the temperature at room temperature (about 20° C.)
2) rapid heating without heating-ramp control, to 100° C.
3) cooling from 100° C. to −20° C. at a controlled rate of 10° C./min
4) return to room temperature and end of the process.

It will be noted that in this case, when only the crystallization zone is used in the process according to the invention, the lower limit temperature is −20° C., and as such the heat treatment is between −20° C. and 100° C.

This heating/cooling program for obtaining the cooling crystallization peak may be performed in less than 30 minutes per sample.

Each time, a flow of inert gas of 50 ml/min is used during the process; the samples in the crimped capsules, as indicated in the preceding examples, were weighed beforehand to be within the mass zone of 4 to 10 mg. After the measurement, the weight of the capsule is controlled to check that there are no significant losses of mass. The data obtained, namely points (T, Q) for (temperature, heat flow) corresponding to a cooling step, may be analyzed by the "Universal Analysis" computer program of the machine to obtain the crystallization peak temperature, Tc, and the crystallization-start temperature, Td (also known as Tonset). The shape factor, SF, for which the method of obtention by calculation is defined in the preceding examples, may be calculated from the numerical data corresponding to the pairs of values (T, Q). Alternatively, a computer program for calculating the three parameters from experimental data (T, Q) may be used. Such a computer program was developed by the Applicant by using the LAB-VIEW® application.

Numerous experiments and the correlation with other methods for determining the level of crosslinking of EVA encapsulators, as discussed in example 4, made it possible to establish that, for the quality control of the crosslinking, a minimum value criterion to be reached for each of the three parameters Tc, Td and shape factor (Tc, Tonset, SF), made it possible optimally to evaluate the crosslinking quality of the EVA. Thus, for an EVA containing 33% vinyl acetate described in the preceding examples, when Tc, Td (or Tonset) and SF are, respectively, less than or equal to 33° C., 37° C. and 67%, this corresponds to EVA encapsulators that are well crosslinked (in terms of gel contents, for example, this corresponds to EVAs with a gel content of greater than 75%, measured by extraction with xylene according to standard ASTM D-2765-95). These minimum values may be adjusted for each type of EVA used (supplier, grade, optionally a batch), without very different values being expected, as long as the EVA used remains a photovoltaic-grade EVA containing 33% by weight of vinyl acetate. In addition to the case where all three parameters would have values less than or equal to their respective minimum values, two other cases may arise:

a) when the values of the three parameters are, respectively, greater than the minimum values, in this example 33° C., 37° C., 67%, in which case the crosslinking will be considered as unacceptable in a quality control logic b) when one out of three parameters or two out of three parameters do not reach the minimum values: in this case, if it is one parameter out of three, the crosslinking may be considered as passable but to be kept under surveillance, and if it is two parameters out of three, it may be considered as unacceptable for quality control purposes just as when the three parameters do not reach their minimum values.

Table V below presents all of the measurement results for the three parameters Tc, Td (or Tonset) and SF, for all the EVA samples originating from real modules. A code ("yes" or "no") indicates the fact that the parameter under consideration is less than or equal to (yes) its empirical minimum value, or greater than this value (no). In accordance with the rules defined in the preceding paragraph, the final column indicates the final quality control verdict (QC verdict) by a "Passes", "Does not pass" or "Passes. To be kept under surveillance".

TABLE V

Use of the process of the invention for the quality control of photovoltaic modules

| Description of the sample | Tc (° C.) | Td or Tonset (° C.) | SF (%) | Param. 1 | Param. 2 | Param. 3 | QC verdict |
|---|---|---|---|---|---|---|---|
| Non-crosslinked EVA, before lamination | 41.9 | 49.9 | 90.8 | NO | NO | NO | Does not pass |
| Well-crosslinked control EVA derived from a module* | 32.56 | 36.81 | 63.92 | YES | YES | YES | Passes |
| "Suspect" EVA. Doubts regarding the quality of the crosslinking** | 37.98 | 42.46 | 77.13 | NO | NO | NO | Does not pass |
| "Soft" EVA derived from a module with doubts regarding the quality of the crosslinking | 34.13 | 38.53 | 71.17 | NO | NO | NO | Does not pass |
| "Storage time >3 months" EVA. Standard lamination 145° C./10 min* | 32.97 | 37.03 | 64.7 | YES | NO | YES | Passes. To be kept under surveillance |
| "Storage time >3 months" EVA. Shortened lamination 145° C./<10 min* | 33.03 | 36.97 | 67.3 | NO | YES | NO | Does not pass |
| "Storage time >3 months" EVA. Nominal lamination at 150° C./10 min* | 31.29 | 36.07 | 66.11 | YES | YES | YES | Passes |
| EVA from module without glass, composite rear face, extended cycle** | 32.11 | 36.46 | 65.71 | YES | YES | YES | Passes |
| "Storage time >6 months" EVA. Additional layer of EVA. Standard lamination** | 31.42 | 36.09 | 67.52 | YES | YES | NO | Passes. To be kept under surveillance |

*Standard glass/EVA/cells/EVA/fluorinated polymer structure.
**Structure without glass (transparent fluorinated polymer as the front face) and with a rear face of polymer/glass fiber composite.

As expected, the EVA with no crosslinking does not pass any criterion, whereas a suitably crosslinked EVA passes them all. The EVA termed "suspect" does not pass any criterion, just like the EVA termed "soft" even though the values of the parameters for the latter more closely approach the limit values. In this, the method is sensitive to different degrees in the rejected or accepted samples. The EVA in standard lamination with three months of storage passes two criteria out of three and the third is virtually on the minimum value, it may be considered that the crosslinking is passable, but only just. The EVA in shortened lamination with three months of storage passes only one criterion and is rejected, even though it may be observed that it comes very close to the minimum values. In this case, the manufacturer's experience may lead to modifying the acceptance/rejection rules, so as to take into account limit cases such as this one; given the rules defined for this example, the QC verdict for this sample is negative. With an increase of 5° C. (corrective measurement) of the lamination nominal value in a standard cycle, it is found that the EVA once again passes the three criteria. For the last two samples, the main difference is the storage time of the EVA, which has doubled. This is reflected by poorer crosslinking: the sample at three months of storage passes all the criteria, the one at six months passes two criteria out of three and is accepted, but with reservations. These reservations make it possible to trigger corrective actions such as increasing the lamination temperature.

The invention claimed is:

1. A process for characterizing a copolymer of ethylene and vinyl acetate (EVA) using a differential calorimetry analysis technique, wherein said process comprises the steps of:
    subjecting a sample of said EVA copolymer to a heat treatment, by temperature increases and decreases at constant rate, between a lower limit temperature of –80° C. and an upper limit temperature of 120° C., to obtain a thermogram,
    on the thermogram obtained, detecting a temperature zone corresponding to a crystallization temperature zone,
    determining a crystallization peak of the crystallization temperature zone by crossing of two straight lines tangent to a descending slope of a peak in the crystallization temperature zone and a shape factor of said peak,
    comparing said crystallization temperature zone and said crystallization temperature peak with a corresponding crystallization temperature zone and crystallization temperature peak on reference thermograms obtained from samples of EVA with known cross-linking densities, or with a corresponding temperature zone and crystallization temperature peak on thermograms of other samples obtained from samples of EVA with unknown cross-linking densities, wherein the reference thermograms and thermograms of other samples are obtained using the same heat treatment as the sample of EVA copolymer is subjected to, and
    determining at least one characteristic value of said sample of EVA copolymer selected from the group consisting of a degree of crosslinking of said sample and vinyl acetate content of said sample, based on said comparison.

2. The process as claimed in claim 1, wherein, on the thermogram obtained, a glass transition temperature zone and a melting temperature zone are detected to be compared, respectively, with a corresponding zone of glass transition temperatures or of melting temperature on the reference thermograms or on the thermograms of the other samples.

3. The process as claimed in claim 2, wherein said melting temperature zone is in the form of a melting peak, and in that prior to the comparison step, an additional step of characterization of said melting peak comprises determining a minimum temperature of said melting peak.

4. The process as claimed in claim 1, wherein the lower limit temperature is –20° C. and the upper limit temperature is 100° C.

5. The process as claimed in claim 1, wherein the at least one characteristic value of said sample of EVA copolymer also includes fluidity or molecular mass of said sample.

6. The process as claimed in claim 1, wherein said heat treatment applied to said sample comprises the following steps:
    a) cooling the sample to the lower limit temperature, and, when said lower limit temperature is equilibrated, maintaining the sample at said temperature for at least a predetermined time,
    b) heating said sample up to the upper limit temperature,
    c) repeating steps a) and b) at least once,
    d) cooling said sample to room temperature.

7. The process as claimed in claim 6, wherein the cooling and heating are performed at a constant rate of between 5° C./min and 20° C./min.

8. The process as claimed in claim 6, wherein prior to the comparison step, an additional step of eliminating from the thermogram of the EVA copolymer, information corresponding to the first cooling, step a, and to the first heating, step b, of said heat treatment applied to said sample.

9. The process as claimed in claim 1, wherein the shape factor determines a shape of said peak and is obtained by:
    determining a maximum temperature (Tc) of the crystallization peak,
    determining calculation limits at temperatures encompassing the descending slope of the crystallization peak,
    within said determined calculation limits, plotting a curve representing a ratio of temperature to heat flow (T/HF) as a function of temperature, and then
    on the curve thus plotted, determining a maximum value [max(T/HF)] of said ratio, and finally
    calculating a shape factor SF value according to the following formula:

$$SF = \frac{\max(T/HF)}{Tc/\min(HF \text{ at } (Tc\text{-}X \text{ °C.}))} * 100;$$

in which min (HF at (TC–X° C.)) represents a minimum value of heat flow at a low calculation limit temperature of the calculation limits.

10. The process as claimed in claim 9, wherein the calculation limits encompassing the descending slope of the crystallization peak are defined by the maximum temperature (Tc) of said peak and by a low limit temperature equal to said maximum temperature (Tc) decreased by 20° C.

11. A differential calorimetry analysis device comprising a supervision module arranged to control the steps of the process as claimed in claim 1.

12. A computer program comprising program code instructions for executing the steps of the characterization process as claimed in claim 1, when said program is executed by a processor.

13. A process for determining quality of an EVA copolymer used in the manufacture of cables, which comprises collecting a sample with a mass of between 2 and 15 mg of said copolymer and subjecting said sample to the steps of the characterization process as claimed in claim 1.

14. A process for determining quality of an EVA copolymer used in the manufacture of a photovoltaic module, which comprises collecting a sample with a mass of between 2 and 15 mg of said copolymer and subjecting said sample to the steps of the characterization process as claimed in claim 1.

15. A process for determining resistance over time of an EVA copolymer used in the manufacture of a photovoltaic module, which comprises collecting from a photovoltaic module which has aged, a sample with a mass of between 2 and 15 mg of said copolymer and subjecting said sample to the steps of the characterization process as claimed in claim 1.

* * * * *